United States Patent [19]

Wright

[11] Patent Number: 5,397,820

[45] Date of Patent: Mar. 14, 1995

[54] MONOMERIC HINDERED AMINE ESTERS OF MONOCARBOXYLIC RESIN ACID AND OLEFIN POLYMER COMPOSITIONS STABILIZED THEREWITH

[75] Inventor: Charles M. Wright, Wilmington, Del.

[73] Assignee: HIMONT Incorporated, Wilmington, Del.

[21] Appl. No.: 934,884

[22] Filed: Aug. 24, 1992

Related U.S. Application Data

[62] Division of Ser. No. 769,028, Sep. 30, 1991, Pat. No. 5,169,949.

[51] Int. Cl.$^6$ .................... C08K 5/3435; C08L 93/04
[52] U.S. Cl. ...................... 524/99; 524/270; 524/274
[58] Field of Search .................... 524/99, 270, 274

[56] References Cited

U.S. PATENT DOCUMENTS

| | | | |
|---|---|---|---|
| 3,840,494 | 10/1974 | Murayama et al. | 524/99 |
| 4,046,737 | 9/1977 | Holt et al. | 524/99 |
| 4,101,508 | 7/1978 | Minagawa et al. | 524/99 |
| 4,233,410 | 11/1980 | Rody et al. | 525/123 |
| 4,500,446 | 2/1985 | Durmis et al. | 546/242 |
| 4,691,015 | 9/1987 | Behrens et al. | 544/198 |
| 4,775,496 | 10/1988 | Wideman et al. | 530/221 |
| 4,946,879 | 8/1990 | Wideman et al. | 524/93 |

FOREIGN PATENT DOCUMENTS

| | | |
|---|---|---|
| 0065655 | 12/1982 | European Pat. Off. |
| 0300160 | 1/1989 | European Pat. Off. |
| 2258752 | 6/1972 | Germany |

*Primary Examiner*—Tae H. Yoon

[57] ABSTRACT

Disclosed are monomeric hindered amine esters of monocarboxylic resin acids and olefin polymer compositions stabilized therewith.

8 Claims, No Drawings

MONOMERIC HINDERED AMINE ESTERS OF MONOCARBOXYLIC RESIN ACID AND OLEFIN POLYMER COMPOSITIONS STABILIZED THEREWITH

This application is a division of application Ser. No. 07/769,028, filed Sep. 30, 1991, now U.S. Pat. No. 5,169,949.

FIELD OF THE INVENTION

This invention relates to the chemical arts. More particularly, this invention relates to novel compounds useful as stabilizers in olefin polymer compositions and to the olefin polymer compositions stabilized therewith.

BACKGROUND OF THE INVENTION

Olefin polymers formed by the polymerization of olefin monomers in the presence of a Ziegler-Natta catalyst have a high degree of crystallinity and beneficial physical properties which make them particularly useful in the production of molded articles, films and fibers. Ziegler-Natta catalysts are formed by the reaction of an inorganic compound of a metal of Groups IV-VIII of the Periodic Table, such as titanium metal tetrahalide. Olefin polymers which are both stereoregular and sterospecific are formed by the polymerization of olefin monomers in the presence of certain Ziegler-Natta type catalysts. Typically the crystallinity is from about 20 to about 90% as determined by X-ray diffraction.

Notwithstanding the very desirable and beneficial properties of these olefin polymers, they are quite susceptible to degradation due to prolonged exposure to sunlight or other sources of ultraviolet radiation. Hence, a number of stabilizers have been developed over the years which tend to inhibit the degradation of these olefin polymers. However, these stabilizers suffer from one or more deficiencies. For example, they have an adverse effect on the physical properties of the olefin polymers during processing, or they fail to provide a product which has any appreciable storage stability due to limited compatibility with olefin polymers.

U.S. Pat. No. 4,233,410 describes oligomeric or polymeric polyalkylpiperidine derivatives manufactured by a poly-condensation reaction or polyaddition reaction as polymeric light stabilizers. The polymeric light stabilizers have an average degree of polymerization of 2 to 50 and a molecular weight of up to 10,000, polymers having an average molecular weight of from 1,000 to 6,500 are exemplified.

Polymers and copolymers of an unsaturated carboxylic acid ester containing at least one 2,2,6,6-tetraalkyl piperidyl group in the molecule or a copolymer of said unsaturated carboxylic acid ester with another copolymerizable unsaturated monomer containing a 2,2,6,6-tetraalkyl piperidyl group having a molecular weight of 1,000 to 20,000 as polymeric light stabilizers are disclosed in EP 65655.

U.S. Pat. Nos. 4,775,496 and 4,946,879 describe antidegradants for rubber compounds consisting of the reaction product of a rosin acid and a polyfunctional compound having at least one functional group capable of reaction with a carboxylic acid functionality and another functional group having antidegradant properties selected from the group consisting of 4-hydromethyl-2,6-di-t-butylphenol, 4,4'-methylenebis-(2,6-di-t-butylphenol), 4,4'-butylidenebis-(6,-t-butyl-3-methylphenol), 4,4'-thiobis(6-6-butyl-m-cresol), 4,4'-thiobis(6-t-butyl-o-cresol), 2-mercaptobenzimidazole, p-aminodiphenylamime, p-hydroxy-diphenylamine, p-hydroxy-p'-amine-diphenylamine and p,p'-diamino-diphenylamine.

SUMMARY OF THE INVENTION

This invention provides a new class of stabilizers for olefin polymers which inhibit the degradation resulting in loss of mechanical properties and discoloration of olefin polymers, and which are compatible with olefin polymers and miscible With solvents typically used in "in-process" stabilization. These new stabilizers are monomeric esters of monocarboxylic acids commonly referred to as resin acids. The monomeric esters have the general formula of:

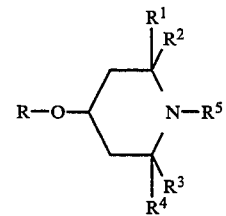

wherein R is a saturated or unsaturated carboxyl radical having 20 carbon atoms (including the carbon of the carboxyl), $R^1$, $R^2$, $R^3$ and $R^4$ are the same or different $C_{1-8}$ linear or branched alkyl radical and $R^5$ is hydrogen or $C_{1-8}$ linear or branched alkyl.

This invention further relates to olefin polymer compositions stabilized with an effective amount of the monomeric esters having the general formula.

DETAILED DESCRIPTION OF THE INVENTION

All percentages are by weight unless otherwise indicated. Ambient or room temperature is approximately 25° C.

In the above general formula, typical R radicals include abietyl, neoabietyl, tetrahydroabietyl, dehydroabietyl, dihydroabietyl, pimaryl, levopimaryl, dextropimaryl, isodextropimaryl, tetrahydropimaryl, dextropimaryl and mixtures thereof; and suitable $R^1$, $R^2$, $R^3$, $R^4$ and $R^5$ alkyl groups include methyl, ethyl, propyl, isopropyl, tertiarybutyl, 2-methylbutyl, 3-methylbutyl, 2-ethylbutyl, 3-ethylbutyl, 2-methyl-3-ethylbutyl, 2-methylpentyl, 3-methylpentyl, 2-ethylpentyl, 3-ethylpentyl, 2-methyl-3-ethylpentyl, 2-methylhexyl, 3-methylhexyl, 4-methylhexyl, 2-ethylhexyl, 3-ethylhexyl, 4-ethylhexyl, 2-methylheptyl, 3-methylheptyl, 4-methylheptyl, and 5-methylheptyl.

Preferably, the monomeric esters of this invention are prepared by reacting a resin acid material or mixtures thereof with a thionyl chloride, and reacting the resultant intermediate with a piperidinol, in the presence of a solvent. An alternative method is the transesterification of the ester of the resin acid with a piperidinol, in the absence or presence of a solvent.

The monomeric esters of the present invention have a molecular weight of from 300 to 500.

Resin acids are found in wood rosin, gum rosin and tall oil rosin. Resin acids are typically classified either as an abietic type or a primaric type according to the distinguishing features set forth in Encyclopedia of Chemical Technology, Vol. II, 779, 786-87 (1953). Hence, resin acids useful in the practice of this invention include abietic acid, neoabietic acid, dehydroabietic acid, dihydroabietic acid, tetrahydroabietic acid, palustric acid, pimaric acid, levopimaric acid, dextropimaric acid isopimaric acid, dihydropimaric acid and tetrahydropimaric acid. Mixtures of these acids can be used.

The individual resin acids may be used as isolated entities. Techniques for isolating resin acids are described in the aforementioned Encyclopedia of Chemical Technology reference, page 484.

Hydrogenated resin acid materials and mixtures thereof can also be used and are preferred. As used herein, the term "hydrogenated resin acid material" means any resin acid material in which the ethylenic unsaturation of the resin acids thereof are partially or substantially completely hydrogenated. Typically a partially hydrogenated resin acid material is hydrogenated to the extent that 40 to 60% of its total ethylenic unsaturation has been saturated. A substantially completely hydrogenated resin acid material usually has greater than 60% up to about 98%, preferably about 65% to about 95%, most preferably about 65% to 90% of its total ethylenic unsaturation saturated with hydrogen. Substantially completely hydrogenated resin acid materials are generally referred to by the manufactures of same as highly hydrogenated resin acid materials which are available commercially. Typically the resin acids useful in the practice of this invention have a bromine number from 5 to 28.

Hence, the resin acid material may be a resin acid or a hydrogenated derivative thereof, or any combination of mixture of such resin acid materials.

Preferred alkyl-substituted piperidinol compounds include 2,2,6,6-tetramethyl-4-piperidinol and 1,2,2,6,6-pentamethyl-4-piperidinol. The piperidinol compounds are commercially available or can be prepared by known methods.

Suitable solvents for the preparation of the esters include triethylamine, methylene chloride and toluene. Triethylamine is the preferred solvent.

Olefin polymers which can be stabilized by the esters of this invention are those prepared by the polymerization of $C_{2-10}$ olefin monomers or the copolymerization or terpolymerization of one such olefin monomer with a different or two different, as the case may be, such olefin monomers, which polymers have a crystallinity or semi-crystallinity, as determined by X-ray diffraction, of from 20 to about 90%.

The preferred olefin polymer is a propylene polymer material. Suitable propylene polymer materials include (a) a homopolymer of propylene; (b) a random copolymer of propylene and an olefin selected from the group consisting of ethylene, and $C_4$-$C_{10}$ alpha-olefins, provided that, when the olefin is ethylene, the maximum polymerized ethylene content is about 10, preferably about 4, percent by weight, and, when the olefin is a $C_4$-$C_{10}$ alpha-olefin, the maximum polymerized content is about 20, preferably from about 16, percent by weight; (c) a random terpolymer of propylene and an olefin selected from the group consisting of ethylene and $C_4$-$C_8$ alpha-olefins, provided that the maximum polymerized $C_4$-$C_8$ alpha-olefin content is about 20, preferably about 16, percent by weight, and when ethylene is one of the olefins, the maximum polymerized ethylene content is about 5, preferably about 4, percent by weight; or (d) a homopolymer of (a) or a random copolymer of (b) which is impact-modified with an ethylene-propylene rubber in a reactor or series of reactors in the presence of (a) or (b) as well as by physical blending (a) or (b) with the rubber until a homogeneous blend is obtained. The ethylene-propylene rubber content of (d) being from about 5 to about 40% and the ethylene content of said rubber being from about 7 to about 60%, preferably from about 10 to about 40%.

The $C_4$-$C_{10}$ alpha-olefins include the linear and branched $C_4$-$C_{10}$ alpha-olefins such as, for example 1-butene, 1-pentene, 3-methyl-1-butene, 4-methyl-1-pentene, 1-hexene, 3,4-dimethyl-1-butene, 1-heptene, 3-methyl-1-hexene, and the like.

Propylene homopolymers and random copolymers of propylene are most preferred.

In general 0.005 to 3%, by weight of the olefin polymer, of the ester stabilizer of this invention can be used to stabilize olefin polymers and compositions based on olefin polymers. Typically, 0.01 to 0.5 is used, preferably 0.01 to 0.3 is used, most preferably to 0.05 to 0.25%.

The stabilizers of this invention do not need a costabilizer. However, stabilizers, such as distearyl thiodipropionate (DSTDP), dilauryl thiodipropionate (DDLTDP), tris(2,4-di-tert-butylphenyl)phosphite, tetrakis[methylene 3-(3',5'-di-tert-butyl-4'-hydroxyphenyl)propionate]methane, 1,3,5-tris(3,5-di-tert-butyl-4-hydroxybenzyl)isocyanurate or a stabilizer composition the main component of which is tetrakis(2,4-di-tertbutyl-phenyl)-4,4'-biphenylene diphosphonite and tris(4-nonyl-phenyl)-phosphite (TNPP), can be used in addition to the stabilizer of this invention. If such stabilizers are used, they typically are present in an amount of from 0.01% to 0.30% by weight of total composition.

In addition, the polyolefins may contain other conventional additives such as antacids, peroxides, pigments and fillers.

The following examples illustrate the preferred embodiments of the instant invention.

EXAMPLE 1

This example illustrates a monomeric ester of this invention and a process for making the same.

Into a reaction vessel equipped with a mechanical stirrer, condenser and nitrogen sparge are added 100 grams (326 mmol) Foral HH tetrahydroabietic acid (a highly hydrogenated resin material from Hercules Incorporated) having a bromine number of 5 and 55 grams (462 mmol) thionyl chloride which is dissolved in 500 ml carbon tetrachloride, and are heated under nitrogen at reflux temperature for five hours. The carbon tetrachloride and unreacted thionyl chloride are then distilled off under reduced pressure to yield 97 grams (92%) of tetrahydroabietic acid chloride as a light brown oil.

Into a second reaction vessel equipped with a mechanical stirrer, thermometer, dropping funnel, nitrogen inlet tube and condenser are added 50 grams (154 mmol) of tetrahydroabietic acid chloride obtained above, 31.5 grams (200 mmol) 2,2,6,6-tetramethyl-4-piperidinol and 7.3 grams (72 mmol) triethylamine which is dissolved in 250 ml toluene under nitrogen. The mixture is heated under stirring to reflux temperature and 18.8 grams (186 mmol) triethylamine are added dropwise over a period of thirty minutes. The heating is maintained for an additional six hours, and then, after cooling, the slurry is filtered off to separate triethylamine hydrochloride. The solid is washed with two portions of 100 ml of toluene. The combined toluene solutions are evaporated under vacuum to yield 62 grams of glassy low melting solid of 2,2,6,6-tetramethyl-4-piperidinyl tetrahydroabietate.

EXAMPLE 2

The procedure and ingredients of Example 1 are used except that Foral AX abietic acids (a mixture of tetrahydro, dihydro and dehydro abietic from Hercules Incorporated) having a bromine number of 26 is used instead of Foral HH tetrahydroabietic acid. 68 grams of 2,2,6,6-tetramethyl-4-piperidinyl tetrahydroabietate and isomers are obtained.

EXAMPLE 3

Into a reaction vessel equipped with magnetic stirrer and condenser, is added 64.3 grams (408 mmol) 2,2,6,6-tetramethyl-4-piperidinol, 64.4 grams of 47% aqueous formaldehyde and 16.8 grams of formic acid. The mixture is heated at reflux temperature for approximately seven hours. After cooling to room temperature, 100 ml of 10M aqueous KOH solution is added to the mixture with stirring. The stirring is stopped and the mixture is separated into two layers. The organic layer quickly solidified into a white crystalline mass. Ether is added to the solid mass until complete dissolution. The organic phase is separated and recovered, and the aqueous phase is washed three times with ether. The combined organic solutions are evaporated to yield a white solid which is further dried under high vacuum at room temperature for three hours. 65 grams of 1,2,2,6,6-pentylmethyl-4-piperidinol, a 93% yield, are obtained.

In a second reactor vessel, under nitrogen, 29.7 grams (173 mmol) of 1,2,2,6,6-tetrapenta-4-piperidinol obtained above, 55 grams (169 mmol) of Foral HH tetrahydroabietic acid chloride prepare as described above in Example 1, and 19 grams (188 mmol) of triethylamine are dissolved in 300 ml of toluene. The reaction mixture is heated at the reflux temperature for six hours, then cooled to room temperature and filtered. The solid is washed twice with 200 ml of ether. The combined ether solutions are washed twice with water, dried over sodium sulfate and evaporated to yield 67 grams of 1,2,2,6,6-pentamethyl-4-piperidinyl tetrahydro-abietate.

EXAMPLE 4

The procedure and ingredients of Example 3 are used except that Foral AX abietic acids (a mixture of tetrahydro, dihydro and dehydro abietic acids from Hercules Incorporated) having a bromine number of 26 is used instead of Foral HH tetrahydroabietic acid. 70.9 grams are obtained of a mixture of 1,2,2,6,6-pentamethyl-4-piperidinyl tetrahydroabietate.

In Examples 5 and 6 the weight percents of the stabilizers used are based on equivalent molar ratio of the active hindered amine functionality of the invention compounds and the comparative compounds.

EXAMPLE 5

This example illustrates the use of the monomeric esters of this invention as UV stabilizers in a propylene polymer.

The esters of Example 1, 2, 3, and 4 and two conventional stabilizers, Tinuvin 765 bis(1,2,2,6,6-pentamethyl-4-piperidinyl)sebacate and Tinuvin 770 bis(2,2,6,6-pentamethyl- 4-piperidinyl)sebacate, are melt compounded with 100 parts of Profax 6801 propylene homopolymer having a nominal melt flow rate of 0.3 dg/min, 0.1 parts of calcium stearate, 0.05 parts of Irganox B225 stabilizer composition blend of tris(2,4-di-t-butylphenyl)phosphite and tetrakis[methylene 3-(3',5'-di-tert-butyl-4'-hydroxyphenyl)propionate]methane, in the amounts as set forth below in Table I until a homogeneous mixture is formed. The mixture is then injection molded into microtensile bars using ASTM #3 mold. The UV radiation is carried out by exposing the bars to Xenon light for 1000, 2000 and 3000 hours according to HIMONT Test Method HI/R&DC-204, available-from HIMONT Incorporated.

TABLE I

| Ingredients | | | | | | |
|---|---|---|---|---|---|---|
| Profax 6801 resin | 100 | 100 | 100 | 100 | 100 | 100 |
| Calcium Stearate | 0.1 | 0.1 | 0.1 | 0.1 | 0.1 | 0.1 |
| Irganox B225 stabilizer | 0.05 | 0.05 | 0.05 | 0.05 | 0.05 | 0.05 |
| Ex. 1 | 0.1 | — | — | — | — | — |
| Ex. 2 | — | 0.1 | — | — | — | — |
| Ex. 3 | — | — | 0.1 | — | — | — |
| Ex. 4 | — | — | — | 0.1 | — | — |
| Tinuvin 765 stabilizer | — | — | — | — | 0.05 | — |
| Tinuvin 770 stabilizer | — | — | — | — | — | 0.05 |
| Tensile Strength | | | | | | |
| @0 Xenon Hours | 7850 | 7600 | 7575 | 7675 | 7775 | 7600 |
| @1000 Xenon Hours | 8400 | 8275 | 8075 | 7975 | 6775 | 6500 |
| % Retention | 107 | 109 | 107 | 104 | 87 | 86 |
| @2000 Xenon Hours | 8000 | 8050 | 8125 | 7950 | 8275 | 8100 |
| % Retention | 102 | 106 | 107 | 104 | 106 | 107 |
| @3000 Xenon Hours | 8550 | 6523 | 8500 | 8050 | 8100 | 8000 |
| % Retention | 109 | 86 | 112 | 105 | 104 | 105 |

The results set forth in Table I show that polypropylene which is stabilized with the monomeric esters of this invention maintain comparable UV stabilization as compared to polypropylene stabilized with the conventional UV stabilizers over the extended test period indicated above.

EXAMPLE 6

To illustrate the radiation resistance of the monomeric esters of the present invention.

The formulation and procedure as set forth in Example 5 are used except that DHT-4A dihydrotalcite antacid is used instead of calcium stearate and Irganox B225 and the resulting blends are extruded into 40 ml sheets.

All of the sheets prepared from the formulations are exposed to cobalt 60 gamma radiation at two different dose levels, i.e., 3 Mrad and 5 Mrad. After radiation, the color is measured on some of the sheets according to ASTM D1925-70, Section I, using a Hunter D25P-2 colorimeter in the total transmission mode (which is first standardized using air as a reference). Yellowness is defined as the deviation on chroma from whiteness in the dominant wavelength range from 570 to 580 nm. The Yellowness Index is a measure of the magnitude of yellowness relative to magnesium oxide standard reference. The lower the number the better the color. The remainder of the irradiated sheets are aged at 60° C. and are tested for impact strength (Gardner) at selected intervals after irradiation over periods of up to 53 weeks. The same formulations in the unirradiated condition are evaluated according to the same procedure. An impact strength of 2.0 in-lb or less is considered a failure. The typical impact strength of unirradiated samples is 30–35 in-lb.

TABLE II

| Ingredients | | | | | |
|---|---|---|---|---|---|
| Profax 6801 resin | 100 | 100 | 100 | 100 | 100 |
| DHT-4A antacid | 0.04 | 0.04 | 0.04 | 0.04 | 0.04 |
| Ex. 1 | 0.05 | — | — | — | — |
| Ex. 2 | — | 0.05 | — | — | — |
| Ex. 4 | — | — | 0.05 | — | — |
| Tinuvin 765 stabilizer | — | — | — | 0.1 | — |
| Tinuvin 770 stabilizer | — | — | — | — | 0.1 |
| Radiation Dose | Days To Failure/Yellowness Index | | | | |
| 0 MRad | >364/1.9 | >364/1.9 | >364/1.9 | >364/1.7 | >364/1.6 |
| 3 MRad | 84/2.7 | 84/2.8 | >364/2.5 | 112/2.3 | 84/2.3 |
| 5 MRad | 7/2.8 | 7/3.3 | 7/2.7 | 0/2.5 | 0/2.6 |

The results set forth in Table II show that the polypropylene which is stabilized with the monomeric esters of this invention maintain comparable radiation resistance as compared to polypropylene which is stabilized with the conventional stabilizers at 3 Mrad, and better resistance at 5 Mrad. No significant differences were seen in the Yellowness Index.

EXAMPLE 7

This example illustrates the solubility of a monomeric ester of this invention in a propylene polymer.

The ester of Example 1 and Tinuvin 770 bis(2,3,6,6-tetramethyl-4-piperidinyl)sebacate set forth in Table III are melt compound with 35 g of Pro-fax 6300 crystalline homopolymer of propylene having a nominal melt flow rate of 10 and a density of 0.903 g/cm³ in a Brabender torque rheometer at 180° C. for 7 minutes and 60 rpm until a homogeneous mixture is formed. The mixture is initially cold pressed and then compression molded using a 100 ton Daniel press with electrically heated platens to prepare (5 cm×5 cm×3 mm) additive-containing plaques. The mixture is pressed initially at 180° C. for 2 minutes at zero pressure followed by one minute pressing under full pressure. Then the plaques are cooled to room temperature, approximately for 15 minutes, under full pressure.

The same procedure is used to prepare (5 cm×5 cm×250 μm) additive-free polypropylene films except that no stabilizers are used and 160° C. is used during a one minute preheat time followed by one minute under full pressure.

The solubility is measured using a solubility cell having four stacks as described in Al-Malaika et al., Polymer Degradation and Stability, 32, 321-247, (1991), each stack having three of the additive-free polypropylene films described above, which are heated for 1 hour at 120° C. under nitrogen, sandwiched between two of the additive-containing plaques described above, which are super-saturated with the particular additive at 60° C. The four stacks are placed in the solubility cell between a top and bottom metal casing. Pressure is applied symmetrically by compression springs to remove air bubbles and achieve intimate contact between the layers of the films and the plaques. The solubility cell is then placed in a vacuum oven at 60° C. (+2° C.). The established equilibrium is monitored at intervals. Once the additive concentration in the film layers of a stack reaches a constant value the experiment is terminated. The concentration of the diffusant in the additive-free polymer film of the stack is determined by using a Beckman DU-7 high speed UV/VIS spectrophotometer and a Perkins-Elmer 599 infrared spectrophotometer.

TABLE IV

| | Solubility (wt %) @60° C. (+2° C.) | |
|---|---|---|
| Stabilizer | UV Abs. | IR Abs. |
| Ex. 1 | 1.380 | 1.015 |
| Tinuvin 770 stabilizer | — | 0.64 |

As demonstrated above in Table IV, the solubility of the monomeric ester of the present invention is much higher than the solubility of the conventional stabilizer. Thus, evidencing better compatibility of the monomeric esters of the present invention.

Other features, advantages and embodiments of the invention disclosed herein will be readily apparent to those exercising ordinary skill after reading the foregoing disclosures. In this regard, while specific embodiments of the invention have been described in considerable detail, variations and modification of these embodiments can be effected without departing from the spirit and scope of the invention as described and claimed.

I claim:

1. An olefin polymer composition comprising at least one polymer and an effective stabilizing amount of at least one monomeric ester having the formula:

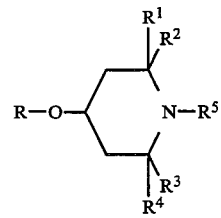

wherein R is a saturated or unsaturated carboxyl radical having 20 carbon atoms selected from the group consisting of abietyl, neoabietyl, tetrahydroabietyl, dehydroabietyl, dihydroabietyl, pimaryl, levoprimaryl, dextropimaryl, isodextropimaryl, tetrahydropimaryl, dihydropimaryl and mixtures thereof, $R^1$, $R^2$, $R^3$ and $R^4$ are the same or are different and are $C_{1-8}$ linear or branched alkyl and $R^5$ is hydrogen or $C_{1-8}$ linear alkyl.

2. The composition of claim 1, wherein the monomeric ester is present in an amount of from 0.005 to 3%, by weight of the olefin polymer.

3. The composition of claim 1, wherein R in the formula of the monomeric ester is tetrahydroabietyl, $R^1$, $R^2$, $R^3$ and $R^4$ are methyl and $R^5$ is hydrogen.

4. The composition of claim 1, wherein R in the formula of the monomeric ester is tetrahydroabietyl, $R^1$, $R^2$, $R^3$, $R^4$ and $R^5$ are methyl.

5. The composition of claim 1, wherein the monomeric ester is present in the amount of from 0.01 to 0.5%, by weight of the olefin polymer.

6. The composition of claim 1, wherein the olefin polymer is a propylene polymer material.

7. The composition of claim 2, wherein the olefin polymer is a propylene polymer material.

8. A useful article comprising the composition of claim 1.

* * * * *